(12) United States Patent
Cichocki et al.

(10) Patent No.: US 8,821,658 B2
(45) Date of Patent: Sep. 2, 2014

(54) THERMAL FORMING OF REFRACTORY ALLOY SURGICAL NEEDLES

(75) Inventors: Frank R. Cichocki, Easton, PA (US); Thomas Nering, Holland Township, NJ (US); David Demarest, Parsippany, NJ (US)

(73) Assignee: Ethicon, Inc., Somerville, NJ (US)

( * ) Notice: Subject to any disclaimer, the term of this patent is extended or adjusted under 35 U.S.C. 154(b) by 70 days.

(21) Appl. No.: 13/439,095

(22) Filed: Apr. 4, 2012

(65) Prior Publication Data

US 2012/0192608 A1 Aug. 2, 2012

Related U.S. Application Data

(60) Continuation of application No. 12/471,524, filed on May 26, 2009, now abandoned, which is a division of application No. 11/756,668, filed on Jun. 1, 2007, now abandoned.

(51) Int. Cl.
| | | |
|---|---|---|
| *C22F 1/18* | (2006.01) | |
| *A61B 17/06* | (2006.01) | |
| *B21J 1/06* | (2006.01) | |
| *C22C 27/04* | (2006.01) | |
| *B21G 1/08* | (2006.01) | |

(52) U.S. Cl.
CPC ... *B21G 1/08* (2013.01); *B21J 1/06* (2013.01); *C22C 27/04* (2013.01); *A61B 17/06066* (2013.01)
USPC .............................. 148/668; 148/673; 606/222

(58) Field of Classification Search
USPC .................. 148/568, 673, 668; 606/223, 222; 72/38, 364
See application file for complete search history.

(56) References Cited

U.S. PATENT DOCUMENTS

| | | | |
|---|---|---|---|
| 1,906,101 A | 4/1933 | Rickey et al. | |
| 2,666,721 A | 1/1954 | Bechtold et al. | |
| 3,573,903 A | 4/1971 | Delgrosso | |
| 3,686,041 A | 8/1972 | Lee | |
| 4,501,312 A | 2/1985 | Matsutani | |
| 5,026,520 A | 6/1991 | Bhowal et al. | |
| 5,411,613 A | 5/1995 | Rizk et al. | |
| 5,415,707 A | 5/1995 | Bendel et al. | |
| 5,437,744 A | 8/1995 | Carlen | |
| 6,077,369 A | 6/2000 | Kusano et al. | |
| 7,001,472 B2 | 2/2006 | Collier et al. | |
| 7,014,722 B1 | 3/2006 | Arimoto et al. | |
| 2001/0001401 A1 | 5/2001 | Segal | |
| 2005/0044922 A1 | 3/2005 | Bogart et al. | |
| 2007/0079984 A1 | 4/2007 | Nakai et al. | |

FOREIGN PATENT DOCUMENTS

| | | |
|---|---|---|
| DE | 3620718 A1 | 12/1987 |
| EP | 0646352 A2 | 5/1995 |
| EP | 0646352 B1 | 6/1998 |
| FR | 1415939 A | 10/1965 |
| FR | 1472637 A | 3/1967 |
| GB | 145739 A | 1/1921 |
| JP | 54155959 A | 12/1979 |

OTHER PUBLICATIONS

Peter L. Raffo "Yielding and Fracture in Tungsten and Tungsten-Rhenium Alloys", NASA Technical Note (NASA TN D-4567) May 1968.
Erik Lassner and Wolf-Dieter, "Tungsten," Kluwer Academic / Plenum Publishers, NY, p. 258, 1999.
Mutoh, et al., "Effects of Rhenium Addition on Fracture Toughness of Tungsten at Elevated Temperatures" Journal of Materials Science, 30 (1995), pp. 770-775.

*Primary Examiner* — Roy King
*Assistant Examiner* — Caitlin Kiechle
(74) *Attorney, Agent, or Firm* — E. Richard Skula

(57) ABSTRACT

A method of thermal forming of refractory alloy suture needles is disclosed. Needle blanks made from refractory alloys are used to form surgical needles, which are heated to a temperature above the ductile to brittle transition temperature but below the recrystallization temperature of the refractory alloy. The heated needle blanks are then mechanically formed into a surgical needle.

18 Claims, 3 Drawing Sheets

THERMAL FORMING OF REFRACTORY ALLOY SURGICAL NEEDLES

CROSS-REFERENCE TO RELATED APPLICATION

This application is a continuation of application Ser. No. 12/471,524 filed on May 26, 2009, now abandoned, which is a divisional of application Ser. No. 11/756,668 filed on Jun. 1, 2007, now abandoned.

This patent application is related to commonly-assigned patent application Ser. No. 11/756,679 filed on evendate herewith, now U.S. Pat. No. 8,062,437, entitled "Thermal Forming of Refractory Alloy Surgical Needles and Fixture and Apparatus", which is incorporated by reference.

FIELD OF ART

The field of art to which this invention pertains is surgical needles, in particular, methods of thermally forming refractory alloy suture needles.

BACKGROUND OF THE INVENTION

Surgical needles are well known in the surgical arts. Typically the surgical needles are mounted to sutures, and used in a variety of surgical procedures for approximating tissue. It is important that the surgical needles function under a variety of conditions encountered by surgeons when performing procedures on patients. Surgical needles can be used for delicate surgical procedures with relatively soft and fragile tissues such as liver or lung surgery and for more robust procedures involving harder and tougher tissues such as ophthalmic, plastic, or coronary artery bypass graft surgery. Surgical needles are also used in various orthopaedic surgical procedures. Surgical needles must be able to penetrate tissue rapidly and efficiently with minimal surgeon insertion force and minimal tissue trauma. It is particularly important that the surgical needle maintain its structural integrity through multiple cycles while tissue is being approximated by the surgeon.

Surgical needles may be made from a variety of materials that have the required strength and manufacturability properties. Examples of these materials include various grades of stainless steel including, 420, 455, 4310 and various grades of specialty martensitic-aged steels including ETHALLOY (Ethicon, Inc., Somerville, N.J.). Although needles made from such conventional materials are capable of adequate performance, there is a constant search for surgical needles having improved properties that will benefit both the surgeon and the patient. Certain refractory metals offer unique properties such as exceptional stiffness and strength that impart desirable handling characteristics to suture needles. However, the room temperature formability of many refractory alloys is limited and often substantially less than the formability of other metals typically used in the manufacture of suture needles. Difficulties may thus arise in the manufacture of refractory alloy surgical needles as numerous steps in a conventional manufacturing process require substantial material ductility. Suture needle bodies are often press-formed or coined to exhibit flattened sides to facilitate grasping and needle orientation within the suture needle drivers. Needle bodies formed to exhibit flattened sides may also impart modest improvements in strength and stiffness to the suture needle. Needle points also may be coined to produce cutting edges desirable for the penetration of certain tissues. Furthermore, needles are commonly curved into a variety of arcuate configurations, for example, ¼, ⅜, or ½ circle designs, in order to facilitate certain surgical procedures. The surgical needles must be processed during manufacturing to provide for the mounting of surgical sutures. One way of mounting sutures to a surgical needle is to drill a blind bore hole into the proximal end of the needle to receive the end of a surgical suture. For channel mounted sutures, as opposed to sutures mounted in a drilled bore hole in the proximal end of the needle, needle channels are typically coined or stamped into the proximal end of the suture needle. In either type of mounting configuration, the proximal ends of the needles are typically swaged to maintain the suture end in the channel or the bore hole.

The forming of refractory alloys into suture needle materials has not been extensively investigated. Conventional needle forming methods typically cannot be used with refractory alloys. For example, it is known to use a method of forming a suture receiving hole in steel needles by pressing a perforating tool into the base of suture needle while the needle material is heated to a temperature close to the melting temperature, Tm, between the hot forming and casting temperature of the alloy. This method is deficient for use on refractory metals for several reasons. If an alloy is taken to a temperature near the melting point of the alloy, recrystallization of the alloy is a distinct likelihood. Indeed recrystallization commonly occurs at much lower temperatures, for many alloys around 0.4 Tm. If refractory metals are heated to near their melting point, recrystallization of the work hardened microstructure occurs and the alloy can be expected to lose essential properties and even exhibit brittle characteristics at room temperature due to the effect of microstructural changes on the ductile to brittle transition temperature, DBTT. Secondly, such a process is applicable to oxidation resistant alloys, however, this is not the case for refractory alloys (especially those in the W—Re binary system) as these alloys will readily oxidize at temperatures far below their melting points.

The previously described needle forming methods may impart substantial stresses to the needle material, and if the material exhibits insufficient ductility, cracking and or splitting of the suture needle may occur. Many refractory alloys exhibit ductile to brittle transition temperatures (DBTT) above room temperature, and consequently the ability to plastically deform these refractory alloys in the various surgical needle forming operations is substantially limited. However, once above the DBTT, plastic deformability of the refractory alloys increases substantially. Excessively high temperatures may however lead to the recrystallization and growth of the grain structure of the alloy, leading to a substantial change in properties that may be deleterious to the performance of the suture needle.

Therefore, there is a need in this art for novel methods of manufacturing and forming refractory alloy suture needles.

BRIEF DISCLOSURE OF THE INVENTION

Accordingly, a novel method of thermal forming refractory alloy suture needles is disclosed. In the method, an alloy metal needle blank is provided. The needle blank is made from a refractory metal alloy. At least a section of the needle blank is heated to a temperature above the ductile to brittle transition temperature but below the re-crystallization temperature of the alloy. The heated needle blank is mechanically formed into a surgical needle.

These and other aspects of the present invention will become more apparent from following description and accompanying drawings.

DETAILED DESCRIPTION OF THE INVENTION

Figure 1:
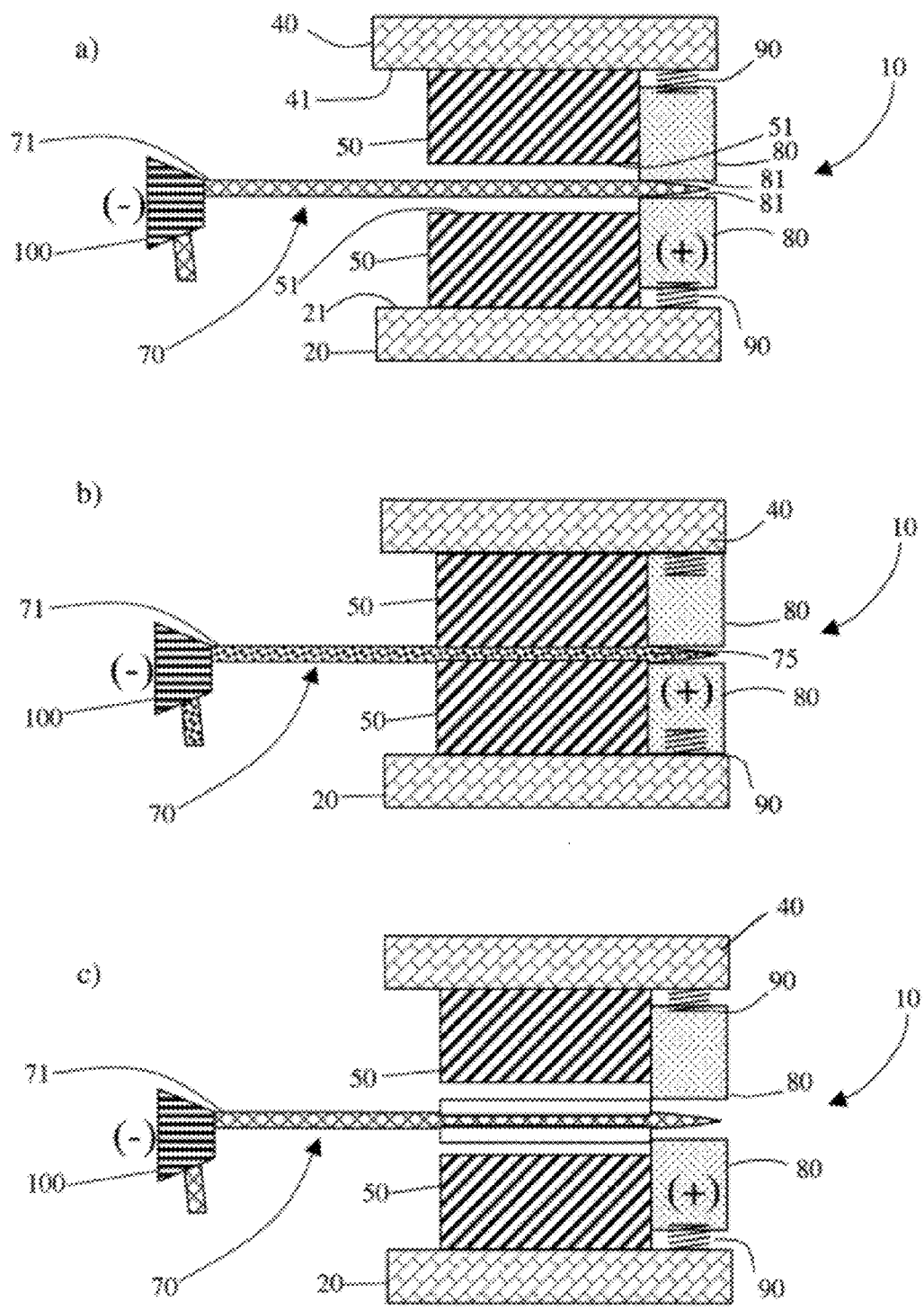
FIGS. 1A-C illustrate a schematic of a thermal forming process of the present invention utilizing resistive heating.

Using the novel thermal forming processes of the present invention, refractory alloys used in the manufacture of suture needles are heated to a temperature above their DBTT during the given forming operation to provide substantial plastic deformation, but below the recrystallization temperature of the alloy to prevent compromise of the suture needle properties. Several methods for the thermal treatment and forming of suture needle materials during needle forming operations are disclosed. Needles manufactured from refractory metal alloys treated using the novel thermal forming treatment processes of the present invention exhibit numerous potential improvements in needle performance including enhanced resistance to bending, pronounced I-beam (i.e., structural) and needle point designs that enhance strength, stiffness and penetration performance, improved ductility and toughness, and in situ coloration via surface oxidation.

The following terms used in present specification are defined to have the following meanings:

Ductile to Brittle Transition Temperature (DBTT)—Temperature above which a substantial improvement in ductility of the alloy occurs. Within this disclosure the DBTT is determined as the temperature at which the alloy exhibits at least 5% elongation to break in a simple tensile test.

Refractory Alloy—alloy comprised of one or more or the elements: W, Mo, Re, Os, Ir, Ta, Nb, Zr, Y that exhibit a DBTT above room temperature.

Recrystallization Temperature—Temperature at which new grains will form in the microstructure of the alloy.

Ductility—ability of an alloy to withstand plastic deformation without breaking.

Elongation to break—measurement of sample percent elongation in a simple tensile test, used to assess alloy ductility.

Simple Tension—tension applied in one dimension with other dimensions being unconstrained.

Thermal forming—plastic forming conducted on a heated work piece.

Needle Blank—elongate piece of wire, a portion of which is converted via a multitude of processes into the shape of a suture needle.

Yield Bending Moment—the amount of moment required to initiate plastic deformation during bend tests (ASTM standard F-1840-98a)

Bending Stiffness (Stiffness in Bending)—resistance to elastic deformation of a curved suture needle.

Elastic Deformation—deformation, strain, or displacement that is recoverable by removing the applied load I-beam Needle Body—any variety of needle body designs that incorporate flattened opposed sides (instead of an entirely rounded design)

Maximum Bending Moment—the greatest moment applied to needle during bend test (ASTM standard F-1840-98a)

Materials Properties—Properties of the material only, derived by testing in a manner in which needle shape and surface properties do not influence data. Examples include: Young's modulus, ultimate tensile strength (when tested in simple tension), and microhardness hardness.

Grain Structure—an assemblage of crystals that share a common atomic periodicity and together as a multitude comprise the needle material.

Dislocation—a line defect within a grain structure that manifests itself as a missing plane of atoms, that is commonly necessary to enable plastic deformation of metals at or near room temperature.

It should be noted the terms "surgical needle" and "suture needle" are used interchangeably herein.

The metal alloys useful in the practice of the present invention include conventionally known refractory metal alloys including: tungsten, tungsten-rhenium, tungsten-osmium, molybdenum, molybdenum-rhenium, molybdenum-zirconium-titanium, iridium, and the like.

Rhenium additions can substantially improve the ductility of W—Re alloys. Published results for arc melted W—Re alloys of varying Rhenium concentration are disclosed in NASA technical publication (NASA TN D-4567) entitled, "Yielding and Fracture in Tungsten and Tungsten-Rhenium Alloys". A tungsten 25% Rhenium alloy exhibited substantial elongation to break near room temperature whereas a pure tungsten sample exhibited no reportable elongation to break. Taking a closer look at the pure tungsten alloy, it was clear that a marked improvement in elongation to break occurred over the temperature range of 520 to 600K. Over this temperature range the alloy transitioned from brittle to ductile. A ductile to brittle transition temperature (DBTT) is often used to demarcate this transition in ductility, and while this nomenclature is the norm in the field of metallurgy, the actually transition in materials performance does not typically occur at a precise single temperature, but rather occurs over a range of temperatures in a polycrystalline sample. The breadth of this DBTT transition region may increase with Rhenium concentration, with high Rhenium alloys showing a gradual slope up in elongation to break with temperature as opposed to the more rapid change of the pure alloy. Nevertheless, it is clear that heat profoundly increases the ductility exhibited by W—Re alloys. According to this NASA report, for a W-25% Re alloy, the room temperature ductility approximately doubles at 500K and approximately quadruples at 700K. For convenience, the author of this NASA study chose the temperature at which the alloy exhibited 5% elongation to break as the ductile to brittle transition temperature (DBTT), or for the W-25% Re alloy, 350K. It should be noted that other factors such as alloy impurities, grain size, and work hardening history can also impact the onset temperature of ductile behavior (and the reported value of the DBTT).

Suture needles are conventionally and most typically formed from wire through a multitude of conventional process steps including: wire straightening, needle blank formation, point coining and/or point grinding, needle body forming, curving, suture receiving hole drilling, or channel forming, polishing, siliconization, and so on. The process steps may include one or more conventional mechanical, chemical, heat treatment, and/or electrical sub-processes. Suture needle forming operations often result in substantial plastic deformation of the needle material. Even alloys with high rhenium concentration exhibit limited plastic deformation with elongation to break values rarely exceeding 7% at room temperature and more commonly less than 5%. This lack of room temperature ductility can limit the shape and design of the suture needle. In particular, suture needles are typically formed to exhibit rectangular cross-sectional shapes in the body or mid-section of the needle. Such a rectangular cross-section facilitates grasping and control of the suture needle with needle holders in addition to imparting a modest increase in strength and stiffness. In order to form a rectangular cross-section, a series of conventional coining operations, by which the needle is partially flattened between two parallel opposing dies, is typically performed. These coining operations can result in deformation strains that exceed the fracture limits of the W—Re alloy at room temperature. Likewise, needle points are conventionally coined using various conventional dies and conventional coining processes and equipment. A variety of conventional point designs may be coined including but not limited to: taper point, cutting edge, or taper-cut varieties. Cutting edge needles generally provide the best tissue penetration performance with minimal tissue trauma. However, unlike taper point or taper cut needles that may be formed via a sequence of grinding processes, cutting edge needles of optimal design require point coining operations that subject the needle material to substantial deformational strains, and consequently cracks in the needle blank can occur if forming is conducted below the DBTT of a refractory alloy. In particular, cutting edge needles with radius hollow cutting edges, as described by Smith et. al in U.S. Pat. No. 5,797,961A, which is incorporated by reference, offer exceptional penetration performance with minimal tissue trauma, but in production must be preformed via a high deformation coining operation. Other cutting edge needle point designs for ophthalmic and micro surgery are similarly complex, and while offering exemplary tissue penetrating performance, also require high deformation coining operations to produce. Finally, channels may be conventionally formed in the proximal end of suture needles to facilitate suture attachment. This approach is particularly applicable to suture needles with wire diameters below ~0.006" that can be exceedingly difficult to mechanically drill or laser drill for the purposes of producing a suture receiving hole. Substantial plastic deformation commonly occurs during needle channel formation, and if a refractory alloy is formed at room temperature below its DBTT cracking will likely occur.

The novel processes of the present invention enhance the formability of refractory metal alloys such as the tungsten alloys for the purposes of producing suture needles. These novel thermal forming processes of the present invention provide that a metal alloy suture needle blank be elevated to a temperature, just prior to or during a forming operation, that exceeds the DBTT (where the DBTT is determined as the temperature at which the alloy exhibits at least 5% elongation to break in a tensile test) but wherein the temperature is less than the recrystallization temperature of the alloy (where the recrystallization temperature is defined for the purposes of this disclosure as any temperature that leads to the formation of new grains in the microstructure of the alloy, during said forming operation). It is important to prevent recrystallization of the alloy, as a recrystallized microstructure will typically exhibit lower tensile strength, and lower yield strength, both of which are adverse to the handling and performance characteristics of the suture needle. Moreover, recrystallization of refractory alloys, in particular tungsten alloys, often leads to the embrittlement of the alloy by further elevating the DBTT as a consequence of the elimination of dislocations that occurs during recrystallization.

While mechanical forming of a refractory metal suture needle blank at elevated temperature may be necessary to prevent fracture, it is not easily accomplished since equipment used in the manufacture of suture needles is expansive in nature employing several specialized forming stations that typically perform individual needle forming operations serially one after the other, and this equipment cannot be, as a whole, subjected to elevated temperature for long without destroying its function. This equipment is typically high speed precision equipment, and excessive heat could cause mechanical breakdowns of mechanical components. As such, heating of the refractory metal needle blank must be limited to a very small section of the equipment where heat resistant or water-cooled tooling can be used. Alternatively the heat used in forming the needle blanks must be managed, for example to be turned on and then turned off with precise timing to heat predominantly the needle and not the surrounding tooling and equipment. Alternatively, the tooling may be actuated in such a way to substantially limit the duration of its exposure to the thermal forming zone.

Figure 2:
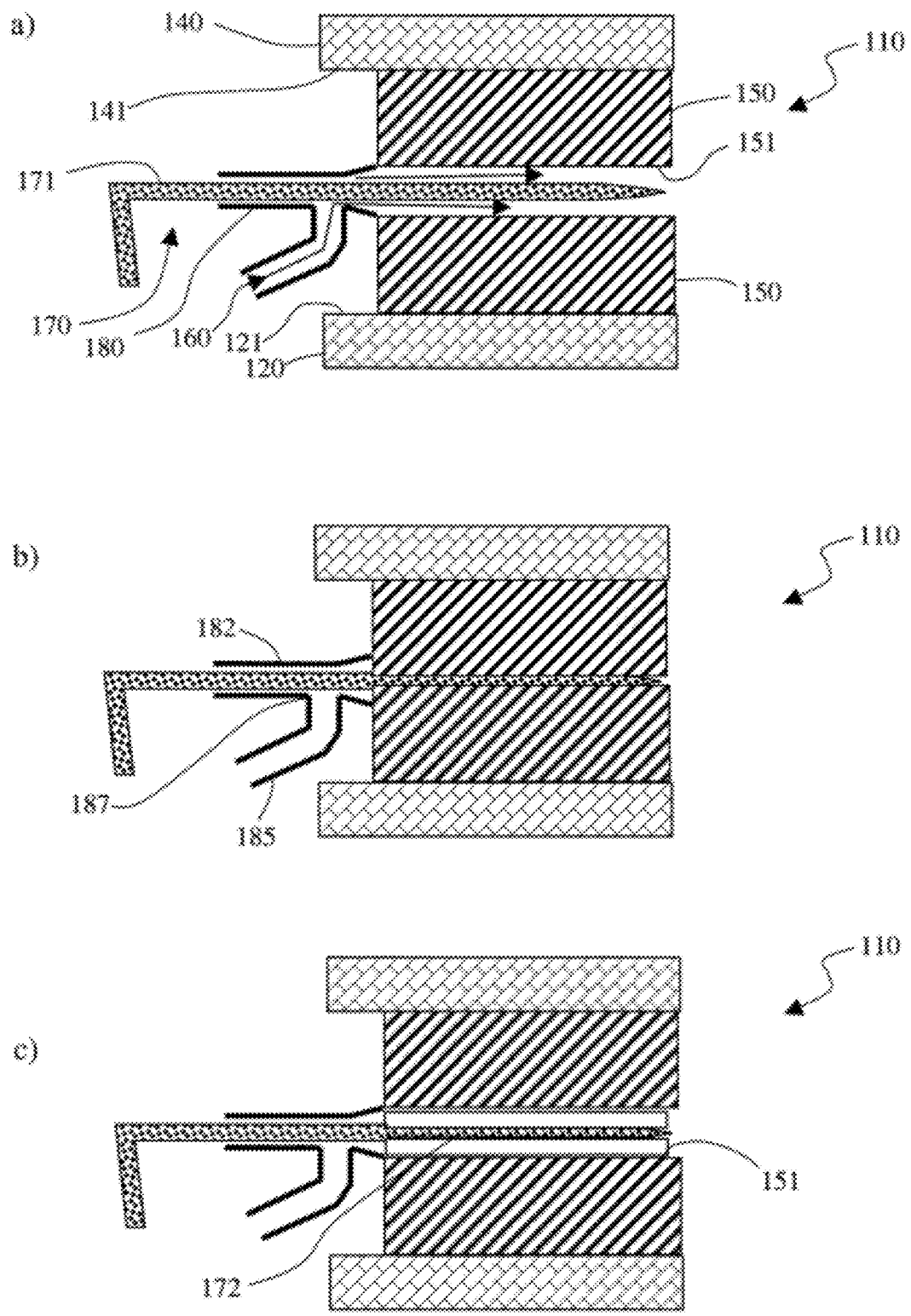
FIGS. 2A-C illustrate an alternate embodiment of the present invention for thermal forming needles from refractory alloys using a hot gas injection system.
Figure 3:
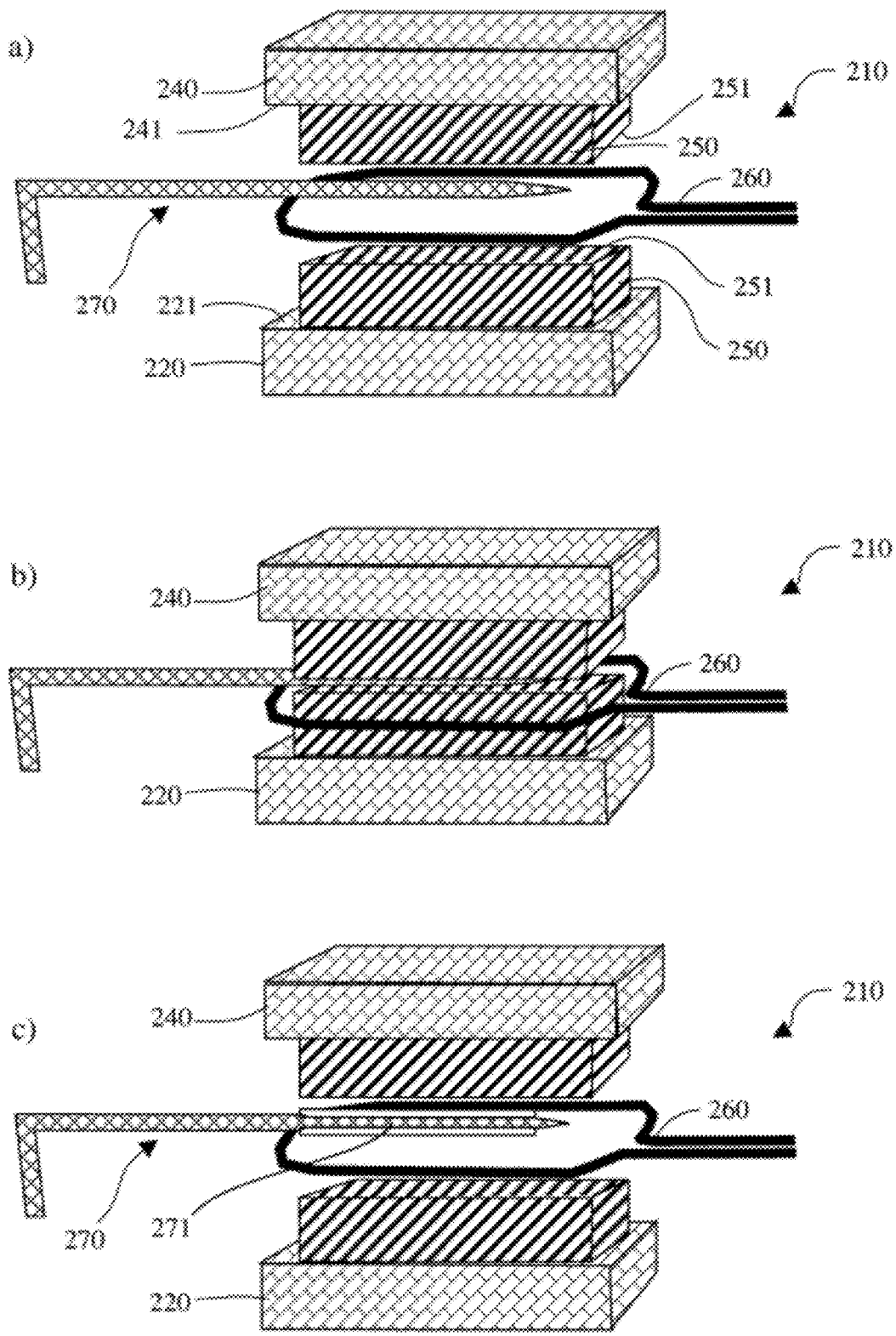
FIGS. 3A-C illustrate yet another alternate embodiment of the present invention for thermal forming of refractory alloy needles using a resistive heating element.

Alternate embodiments of methods of the present invention for thermal forming needles in situ to heat an alloy metal needle blank during or immediately prior to forming are illustrated in FIGS. 1-4, and described herein. These methods include, but are not limited to: 1) resistive needle heating, 2) forced gas needle heating, 3) element controlled needle heating, and 4) laser needle heating.

Referring first to FIGS. 1A-C, a resistive heating embodiment of the process of the present invention is illustrated. The forming die tool 10 is seen to have lower tool base 20 and upper moveable member 40. Mounted respectively to the inner surface 21 of tool base 20 and the inner surface 41 of moveable member 40 are the die members 50 each having inner contact surfaces 51 for engaging the metal alloy needle blank 70. The tool 10 is seen to have a pair of opposed electrodes 80 having contact surfaces 81. The electrodes 80 are moveably mounted via springs 90 to the tool base 20 and moveable member 40, respectively. An electrode 100 is mounted to the proximal end 71 of needle blank 70. In the resistive needle heating process, electrical contact is made across the needle blank from the distal end 75 of needle blank 70 via the electrodes 80 to the proximal end of the needle blank 71 via electrode 100 and current is passed through the needle blank 70 to resistively heat it to the temperature desired for the forming operation. Electrical contact can be made across the length of the needle blank 70 as the needle blank 70 enters the die 10 or as it closes, as seen in FIGS. 1A-C. Alternatively, current maybe passed through the thickness of the needle blank 70 in the section in which forming will occur. Various traditional materials may be used to form the conducting electrodes 80 (e.g. copper) used to make electrical contact and complete the electrical circuit to allow current to pass through the needle blank 70. Optionally, the die members 50 may be used to make electrical contact and conduct the current, as many of the conventional tools such as cemented carbide tools typically used employ a continuous metal binder phase of substantial conductivity. The dies and/or electrical contacts may be optionally liquid cooled to increase their performance and service life. The amount of current passed through the needle blanks 70 in the process of the present invention will be sufficient to effectively heat the needle blank 70 to above its DBTT without inducing recrystallization of the grain structure. The current will depend on wire diameter, composition of the refractory alloy, speed of the die closure, and other dynamic process factors, (and also upon electrical parameters such as voltage, frequency, etc.) but may typically be about 1.0 amp to about 20.0 amps, more typically about 1.0 amp to about 10.0 amps.

Another alternate embodiment of the process of the present invention using a forced gas thermal forming process is illustrated in FIGS. 2A-C. The forming die tool 110 is seen to have lower tool base 120 and upper moveable member 140.

Mounted respectively to the inner surface 121 of tool base 120 and the inner surface 141 of moveable member 140 are the die members 150 each having inner contact surfaces 151 for engaging the metal alloy needle blank 170. With the forced gas method, a stream of hot air or hot gas 160 is directed via guide 180 along the path of the alloy needle blank 170 as it enters and while it is positioned within the die assembly 110 between opposed die members 150. The guide 180 is seen to have needle guide section 182 and gas pathway section 185 that intersect at junction 187. Since the needle blanks 170 are typically small in diameter (between ~1 and 60 mil) rapid convective heating of the needle blank 170 from the forced gas stream 160 may occur. As the needle blank 170 reaches a predetermined forming temperature, the dies 150 close and thermoform a segment 172 of the needle blank 170 to the prescribed shape, as seen in FIGS. 2a-c. The gas used to heat the suture needle may optionally be a shielding gas which would serve to prevent oxidation of the needle during the heating operation. Examples of the gases that can be used include argon, helium, hydrogen, nitrogen, neon, carbon dioxide/carbon monoxide, or mixtures thereof. The velocity of the gas stream and the temperature of the gas stream will be effective to sufficiently heat the refractory alloy above its DBTT while preventing recrystallization. The temperature of the needle during the thermoforming process will be sufficient to effectively enable plastic deformation required in the forming operation without cracking or splitting of the needle blank. The temperature will vary with the alloy selected to manufacture the needle blank. For a W—Re alloy needle blank the temperature will typically range from 100 to about 1900° C., more typically about 300 to about 1600° C., and preferably about 600 to about 1400° C.

Still yet another embodiment of a thermal forming process of the present invention is illustrated in FIGS. 3A-C. The method utilizes a formed resistive heating element. The resistive element may be heated via direct contact to an electrical circuit designed to pass current through the heating element. Alternatively, the resistive heating element may be heated by inductively coupling to a radio frequency magnetic field that in turn induces an alternating current in the element to accomplish resistive heating. Either configuration generates radiant energy from the heating element to heat the suture needle. As seen in FIGS. 3A-C, the forming die tool 210 is seen to have lower tool base 220 and upper moveable member 240. Mounted respectively to the inner surface 221 of tool base 220 and the inner surface 241 of moveable member 240 are the die members 250 each having inner contact surfaces 251 for engaging the metal alloy needle blank 270. A resistive heating element 260 is seen positioned within and about the die assembly in such a way that the heating element 260 fits around the working zone of the die 210, while not interfering with the motion of the needle blank 270 as it enters and leaves the thermal forming zone, and also without interfering with the movement of the die members 250. The heating elements 260 may be electrically or electronically controlled to turn on and off at the appropriate times as the dies open and close to prevent excessive heating of the dies. As seen in FIGS. 3A-C, after the needle blank 270 is heated to a sufficiently effective temperature, the die members 240 engage the needle blank 270 to thermally form a section of the blank 271. Alternatively or in addition to time control of the heating elements, the dies and affected machine components may be optionally liquid cooled to prevent excessive thermal damage. Also, the dies may optionally retract away from the heating element to a position where the temperature does not cause degradation of the die material. As previously described, the heating elements may be of the type that provide radiant heat (as would be the case for standard resistively heated elements, infrared heating elements, and inductively coupled heating elements), or may be in the form of an induction coil wherein the induction coil produces radio frequency that couples directly with and inductively heats the needle blank. If an induction heating element is used, it may be advantageously designed to couple effectively with and heat the needle blank, but not couple with the surrounding dies. The desired temperatures will be those as previously described above for the other thermal heating and forming processes.

Although not illustrated, another thermal forming process of the present invention utilizes laser controlled needle heating. As the name implies, this embodiment uses a focused intense laser light beam to rapidly heat sections of the needle blank that require mechanical forming One or more lasers may impinge upon the needle blank simultaneously to increase the length of the hot zone. The lasers may also be directed back and forth rapidly across the length of the needle that will be formed. Alternatively the needle may be rotated as the laser impinges to increase the heat-affected area.

It will be recognized that as the hot needle blank contacts the lower temperature dies, or as the source of the thermal energy is shut-off, the needle blank will have a tendency to begin to cool. As such, all of the thermal forming processes described above should be designed in such a way that the actual forming operation that results in plastic deformation of the needle material occurs rapidly in comparison to the rate at which the needle blank cools.

As an additional benefit associated with the novel thermal forming methods of the present invention, alloys that may exhibit high DBTT can be formed into suture needles. For example, in the W—Re alloy system, alloys with high rhenium concentrations tend to have lower DBTT than alloys with low rhenium concentration. However, from a commercial perspective, rhenium has a high raw material cost and can be an exceedingly expensive component of the alloy. If the thermal forming methods of the present invention are used, low rhenium concentrations may be used in lieu of high rhenium concentrations to realize a substantial cost savings. An additional benefit is that the market price for the finished suture needle may in theory be reduced, as raw material costs no longer need to be passed on to the customer, and use of the tungsten alloys as suture needle materials may be expanded to a greater number of needle designs.

Furthermore, greater tolerances for impurities in the alloy (that have the effect of elevating the DBTT) may be permissible if the thermal forming methods of the present invention are used. Yet another associated benefit is that supplier availability may broaden, thereby possibly resulting in decreased material cost.

Still yet an additional benefit of use of the novel methods of the present is seen when a needle blank is curved to form a curved or arcuate suture needle with the shape or configuration of, for example, a, ¼, ⅜, ½ circle. During the conventional needle curving process performed at room temperature, residual stresses are typically imparted to the needle body that detrimentally impact the yield bend moment of the needle. It is believed that heat treatment after the curving operation eliminates some or all of such residual stresses and substantially enhances the yielding bend moment of the needle. Thermal forming operations to curve the suture needle at elevated temperatures (e.g. in excess of 900° C.) may result in a similar improvement in yield bend moment.

Heat treating methods for the coloration of refractory alloy suture needles via the formation of a thin native surface oxide may be applied in conjunction with the in situ thermal forming methods of the present invention. Refractory alloy suture needles may thus be colored during needle manufacturing operations, thus eliminating the need for a subsequent thermal coloring step. Where coloration is a desired outcome, the use of a conventional shielding gas should be avoided, or used in combination with a conventional oxidizing gas. However, if coloration is not desired, a shielding gas may be used.

The following examples are illustrative of the principles and practice of the present invention, although not limited thereto.

Example 1

Needle blanks comprised of a tungsten-26% rhenium alloy with a nominal starting wire diameter of 0.203 mm were pressed between two opposing carbide dies to produce parallel opposed body flats. The tungsten-26% rhenium material from which the needle blank was made was acquired from Toshiba Corporation (Yokohama, Japan) and exhibited a breaking strength of 3450 MPa in wire form. A conventional pneumatic uniaxial press was used for the experiments with flat carbide dies. The length of the needle blank, over which body flats were formed, was at least 1 cm. In one set of experiments the needle blanks were pressed to various thicknesses at room temperature and visually examined for cracks at 30× magnification with a stereoscope. It was found that cracks could be formed longitudinally along the length of the wire when the body flat was coined to a thickness equal to or less than ~0.175 mm. In a parallel set of experiments, the W-26% Re needle blanks were resistively heated immediately prior to and during the pressing operation using the experimental configuration similar to that depicted in FIG. 1. A conventional AC variac was used to sufficiently deliver and adjust the current through the needle blank. In this way the needle could be effectively heated to above 1000° C. as evidenced by the yellow to white glow that was produced. The entire heating and pressing operation took ~1.5 seconds. Visual examination at 30× magnification was used to detect cracks. It was found that needles that were heated to above ~1000° C. (yellow to white glow discharge) could be produced with body flats of 0.15 mm or less without any visually detectable cracks.

Example 2

In order to assess the ductility of the suture needles of Example 1, a reshape test was performed wherein each needle was held near its proximal end with suitable, conventional needle holders and bent back and forth through 180 degrees multiple times until fracture of the needle occurred. Each bend though 90 degrees from the initial shape of the needle was given a ½ count. The total number of counts is a measure of ductility with the higher numbers indicating greater ductility. Most suture needles are required by their manufacturers to exhibit a reshape value of at least 1.0. The W-26% Re suture needles made in Example 1 above exhibited reshape values in excess of 4.0 thereby meeting and exceeding the standard requirement.

The novel methods of the present invention for thermoforming surgical needles have numerous advantages and benefits. These advantages and benefits include: production of refractory alloy suture needles with flattened or I-beam body sections, coined needle points, and suture receiving channels without cracking or splitting the needle blank and without compromising ductility and toughness of the suture needle, improved resistance to bending, stiffness, and strength via thermal curving of the suture needle, coloration of the needle surface via native surface oxide formation in situ during thermal forming negating the need for subsequent coloration processes, and selection of lower cost refractory alloys with high DBTT.

Although this invention has been shown and described with respect to detailed embodiments thereof, it will be understood by those skilled in the art that various changes in form and detail thereof may be made without departing from the spirit and scope of the claimed invention.

We claim:

1. A method of forming a refractory alloy into a surgical needle, said method comprising:
    providing a refractory alloy metal needle blank, said needle blank comprising a refractory metal alloy;
    curving the needle blank to have a curved or arcuate shape;
    heating at least a section of the needle blank to a temperature above the ductile to a brittle transition temperature, but below the recrystallization temperature of the alloy; and,
    thermally forming the curved needle blank by plastically deforming the needle blank into a surgical needle at the temperature, wherein the needle is free of cracks and wherein the needle after thermal forming has a reshape value in excess of 1.0.

2. The method of claim 1 wherein the temperature is between about 100° C. to about 1600° C.

3. The method of claim 1 wherein the temperature is between about 600° C. and about 1400° C.

4. The method of claim 1 wherein the elongation to break of the alloy is increased to exceed 5%.

5. The method of claim 1 wherein the forming operation is selected from the group consisting of needle body forming, needle point coining, needle channel coining, and needle curving.

6. The method of claim 1 wherein the alloy has a Rhenium concentration comprising of about 0 wt. % to about 30 wt. %.

7. The method of claim 1 wherein the needle is heated using hot gas jets.

8. The method of claim 1 wherein the needle is heated using a resistive heating element.

9. The method of claim 1 wherein the needle is heated by contacting electrodes to the needle blank and causing an electrical current to flow through the needle blank.

10. The method of claim 1 wherein the needle is in an oxygen free atmosphere when at an elevated temperature.

11. The method of claim 10 wherein the oxygen free atmosphere is a shielding gas or combination of shielding gases selected from the group consisting of nitrogen, argon, helium, and hydrogen.

12. The method of claim 1 wherein the refractory alloy comprises Tungsten and one or more elements selected from the group consisting of Rhenium, Molybdenum, Tantalum, Titanium, Yttrium, Zirconium, and Niobium.

13. The method of claim 1 wherein the refractory alloy comprises Molybdenum and one or more elements selected from the group consisting of Rhenium, Tungsten, Tantalum, Osmium, Iridium, Yttrium, Zirconium, and Niobium.

14. The method of claim 1 wherein the refractory alloy is Tungsten-Rhenium (W—Re).

15. The method of claim 14 wherein the W—Re alloy has a rhenium concentration less than 30 wt. %.

16. The method of claim 14 wherein the temperature of the W—Re alloy is elevated to between 100° C. and 1600° C. where the forming operation is selected from the group consisting of coining, flattening, channel forming, point forming, and curving.

17. The method of claim 1 wherein the alloy needle blank is heated by a method selected from the group consisting of resistive heating, radiant heat, induction coils, and hot gas streams.

18. The method of claim 1, wherein the reshape value is in excess of 4.0.

* * * * *